United States Patent [19]

Regnier et al.

[11] 4,100,286
[45] Jul. 11, 1978

[54] 2-(SUBSTITUTED HETEROCYCLIC AMINE)BENZOIC ACIDS

[75] Inventors: Gilbert Regnier, Chatenay-Malabry; Roger Canevari, Villebon/Yvette; Jean-Claude Poignant, Bures/Yvette; Michel Laubie, Vaucresson, all of France

[73] Assignee: Science Union et Cie, Suresnes, France

[21] Appl. No.: 741,740

[22] Filed: Nov. 15, 1976

[30] Foreign Application Priority Data

Nov. 19, 1975 [GB] United Kingdom ............... 47618/75

[51] Int. Cl.$^2$ .................. A61K 31/505; A61K 31/52; C07D 473/00; C07D 487/04
[52] U.S. Cl. .................................... 424/251; 424/253; 544/277; 544/264; 544/262
[58] Field of Search ................. 260/252, 256.4 F, 254; 424/251, 253

[56] References Cited

U.S. PATENT DOCUMENTS 3,682,918   8/1972   Druey et al. .................. 260/256.4 F Primary Examiner—Paul M. Coughlan, Jr.
Attorney, Agent, or Firm—Gordon W. Hueschen

[57] ABSTRACT

Heterocyclic compounds of the formula:

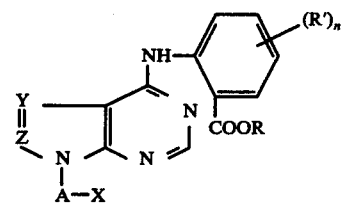

wherein one of Y and Z is CH, the other being N, A is a straight or branched saturated hydrocarbon chain from $C_2$ to $C_6$ inclusive, X is chlorine, hydroxy, alkoxy or alkylthio each from $C_1$ to $C_5$ inclusive, R is hydrogen, alkyl, hydroxyalkyl or dihydroxyalkyl each from $C_1$ to $C_3$ inclusive, R' is halogen, alkyl or alkoxy each from $C_1$ to $C_3$ inclusive and $n$ is 0, 1 or 2.

These compounds, their optical isomers and their physiologically tolerable salts are used as medicines especially in the treatment of central nervous system disorders.

10 Claims, No Drawings

2-(SUBSTITUTED HETEROCYCLIC AMINE)BENZOIC ACIDS

The present invention provides new heterocyclic compounds of the general formula I:

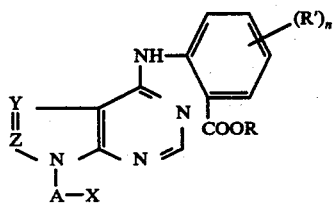

wherein
one of Y and Z is a CH radical and the other is a nitrogen atom;
A is selected from the group consisting of saturated acyclic hydrocarbon radicals having from 2 to 6 carbon atoms inclusive in straight and branched chains;
X is selected from the group consisting of a chlorine atom, a hydroxy radical and alkoxy and alkylthio radicals each having from 1 to 5 carbon atoms inclusive;
R is selected from the group consisting of a hydrogen atom, alkyl, hydroxyalkyl and dihydroxyalkyl radicals each having from 1 to 3 carbon atoms inclusive;
R' is selected from the group consisting of halogen atoms and alkyl and alkoxy radicals each having from 1 to 3 carbon atoms inclusive, and
n is selected from the group consisting of 0, 1 and 2.

The alkyl moieties of the alkoxy and alkylthio radicals represented by X may be for example methyl, ethyl, propyl, butyl or pentyl groups. The alkyl moieties mentioned in the meaning of R and R' may be for example methyl, ethyl or propyl groups. The halogen atoms mentioned in the meaning of R' may be for example fluorine, chlorine or bromine atoms.

The present invention also provides the optically active isomers of the compounds of the formula I wherein A represents a branched saturated hydrocarbon chain. These optical isomers may be obtained starting from the corresponding optically active aminoalcohols such for example as laevo-rotatory and dextro-rotatory amino alcohols from natural amino acids of the S series, such for example as S(+) alaninol or S(+) leucinol.

The compounds of the general formula I in which R is a hydrogen atom are amphoteric substances which may be transformed into addition salts with suitable acids and bases. Among the acids which may be used to form these salts, there may be mentioned for example hydrochloric, hydrobromic, sulfuric, phosphoric, acetic, propionic, maleic, fumaric, tartaric, citric, oxalic, benzoic, isethonic and methanesulfonic acids.

As bases suitable for salt formation, there may be mentioned for example, alkali metal hydroxides and carbonates such as sodium, potassium, and lithium hydroxides and carbonates and organic bases, for example ethanolamine and ethylenediamine.

The compounds of the general formula I in which R is selected from the group consisting of alkyl, hydroxy alkyl and dihydroxyalkyl radicals each having from 1 to 3 carbon atoms inclusive are basic substances which may be transformed into addition salts with suitable acids, for example those mentioned above. All these salts are included in the present invention.

Due to their pharmacological properties the compounds of formula I wherein Y represents a nitrogen atom, Z represents a CH radical, A, X, R, R' and n have the meanings given above, are particularly interesting.

The present invention also provides a process for preparing the compounds of the general formula I which comprises reacting a chloro compound, in a racemic or optically active form, of the general formula II

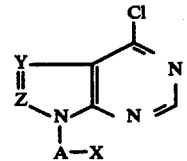

in which Y, Z, A and X have the meanings given above, with an amino compound of the general formula III

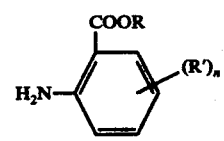

in which R, R' and n have the meanings given above.

Such a process is advantageously carried out by heating an equimolar mixture of the compounds of the formulae II and III in water or in an alcohol/water, dimethylformamide/water, or dimethyl sulfoxide/water mixture, at a temperature of from 50° to 100° C, in the presence of an acceptor for the hydrochloric acid formed during the reaction. As such acceptors there may be mentioned, for example alkali and alkaline earth metal carbonates and hydroxides such as, for example sodium, potassium, and calcium carbonates and sodium and potassium hydroxides.

The starting compounds of the general formula III are known commercial products.

The starting compounds of the general formula II may be prepared according to the methods described in the following examples.

For example the starting compounds of the general formula II'a

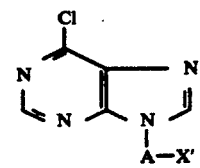

in which A has the meaning given above and X' is a hydroxy, alkoxy or alkylthio radical may be prepared according to the method described by SCHAEFFER and BHARGAVA, Biochemistry (1965), 71, starting from the compounds of the general formula

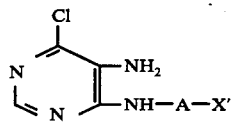

in which A and X' have the meaning given above, which are themselves prepared according to the method described in above mentioned reference or according to the method of IKEHARA et al, J. Amer. Chem. Soc. 83, 2679 (1961).

The starting compounds of the general formula II'b

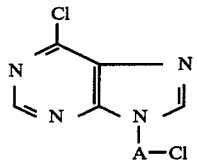

II'b in which A has the meaning given above, may be prepared by chlorinating the corresponding alcohols of the general formula II'a in an excess of SO Cl$_2$. Furthermore, the compound of the general formula II'b in which A is — CH$_2$ — CH$_2$ — may be prepared according to the method described in following Example 1 starting from 4-hydroxy-ethylamino-5-formamido-6-chloropyrimidine.

The starting compounds of the general formula II"a

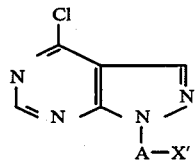

II"a in which A and X' have the meanings given above, may be prepared according to the method described in British Pat. No. 1,284,084, starting from substituted hydrazines of the general formula

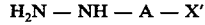

H$_2$N — NH — A — X' in which A and X' have the meanings given above, and 5-formyl-4,6-dichloro pyrimidine which is itself prepared according to the method of KLOETZER and HERBERZ Monatsch. 96 (5), 1567 (1965).

The starting compounds of the general formula II"b

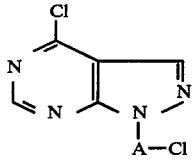

II"b in which A has the meaning given above, may be prepared by chlorinating the corresponding alcohols of the general formula II"a in an excess of SOCl$_2$.

The compounds of the general formula I and physiologically tolerable salts thereof possess valuable pharmacological and therapeutic properties, especially central nervous system depressing, anticonvulsive, myorelaxant and cardiovascular properties.

They may, therefore, be used as medicines, especially in the treatment of disorders of the central nervous system.

Their toxicity is low and their LD$_{50}$ determined in mice varies from 150 to more than 1000mg/kg by the intraperitoneal route.

The activity of the compounds of the present invention on the central nervous system was evidenced by the action of these compounds on the convulsions provoked in mice by electroshock or cardiazole. There were observed inhibitions from 40 to 100% of the tonic convulsive crisis provoked by electroshock with doses which may vary from 5 to 50mg/kg I.P. according to the compounds.

There was also observed in the case of convulsions provoked by cardiazole, an increase of the latent period up to 50% for doses which may lower until 2,5mg/kg I.P. and a protection up to 100% with doses within the range of 10 to 100mg/kg I.P. according to the compounds.

The present invention also provides pharmaceutical compositions containing as active ingredient a compound of the general formula I or a physiologically tolerable salt thereof, in admixture or conjunction with a pharmaceutically suitable carrier, such for example as distilled water, glucose, lactose, starch, talc, magnesium stearate, ethyl cellulose or cocoa butter.

The so-obtained pharmaceutical compositions are advantageously in unit dosage form and may contain from 10 to 200mg of the active ingredient. They may be in form of tablets, dragees, capsules, suppositories or injectable or drinkable solutions and administered by oral, rectal or parenteral route at a dose of 10 to 200mg once to twice a day.

The following Examples illustrate the invention, the melting points being determined in a capillary tube unless otherwise stated.

EXAMPLE 1

2-(9-β-chloroethyl-6-purinylamino)-benzoic acid

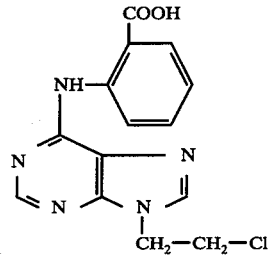

A suspension of 30 g of 9-β-chloroethyl-6-chloropurine (M.P. 107° C) and 38 g of anthranilic acid in 1000 ml of water was heated in the presence of 14.6 g of sodium carbonate. When the temperature reached 60° C there was observed complete dissolution followed by crystallization. The mixture was refluxed for 30 minutes and then cooled and the precipitate was suction-filtered off. After drying, there were obtained 38 g of beige crystals of 2-(9-β-chloroethyl-6-purinylamino)-benzoic acid melting at 187°–188° C.

The starting 9-β-chloroethyl-6-chloropurine was prepared as follows:

There were refluxed, for 3 hours, 234 g of 4-β-hydroxyethylamino-5-formamido-6-chloropyrimidine (M.P. 205° C), in 4.8 l of phosphorus oxychloride.

After the evolution of hydrogen chloride has ceased, the excess phosphorus oxychloride was evaporated under reduced pressure and the residue was poured onto crushed ice. The mixture was alkalized with an excess of potassium carbonate and then the suspension was extracted with 3 l of chloroform. The chloroform solution was washed several times with water and then the chloroform was evaporated off. The pasty residue weighing 135 g was stirred with 500 ml of petroleum ether. The crystals were filtered off, dried, then dissolved in 1800 ml of ethyl acetate. After being stirred for one hour the insoluble residue, weighing 12 g, was filtered off and the filtrate was concentrated under reduced pressure. The resulting residue was washed with petroleum ether. There were obtained 113 g of beige crystals of 9-chloroethyl-6-chloropurine M.P. 107° C (Kofler : 112° C).

The starting 4-β-hydroxyethylamino-5-formamido-6-chloropyrimidine was prepared by heating in 80% formic acid, 4-β-hydroxyethylamino-5-amino-6-chloropyrimidine, M.P. (Koffer) 139° C, itself prepared according to the method of SCHAEFFER and BHARGAVA, Biochemistry (1965) 71.

EXAMPLES 2 - 34

The following compounds were prepared according to the process described in Example 1

(2) ethyl 2-(9-β-chloroethyl-6-purinylamino)-benzoate, M.P. 130°-134° C (anhydrous ethanol), starting from ethyl 2-aminobenzoate and 9-β-chloroethyl-6-chloropurine.

(3) 2-(9-β-hydroxyethyl-6-purinylamino)-benzoic acid, M.P. 295°-300° C (dimethylformamide/ethanol), starting from anthranilic acid and 9-β-hydroxyethyl-6-chloropurine, M.P. 160°-162° C, itself prepared according to the method of SCHAEFFER and BHARGAVA, Biochemistry (1965), 71, starting from 4-β-hydroxyethyl-amino-5-amino-6-chloropyrimidine.

(4) ethyl 2-(9-β-hydroxyethyl-6-purinylamino)-benzoate, M.P. 174°-178° C (anhydrous ethanol), starting from ethyl 2-aminobenzoate and 9-β-hydroxyethyl-6-chloropurine.

(5) 2-[9-(3-hydroxypropyl)-6-purinylamino]-benzoic acid, M.P. (Kofler) 244° C (dioxane), starting from anthranilic acid and 9-(3-hydroxypropyl)-6-chloropurine, M.P. 116°-118° C, itself prepared according to the method of SCHAEFFER and BHARGAVA starting from 4-(3-hydroxypropyl)-amino-5-amino-6-chloropyrimidine prepared according to the method of IKEHARA et al. J. Amer. Chem. Soc. 83, 2679 (1961).

(6) 2-[9-(2-hydroxypropyl)-6-purinylamino]-benzoic acid, M.P. (monohydrate) : 294°-297° C, starting from anthranilic acid and 9-(2-hydroxypropyl)-6-chloropurine, M.P. 101°-103° C, itself prepared according to the method of SCHAEFFER and BHARGAVA starting from 4-(2-hydroxypropyl)-amino-5-amino-6-chloropyrimidine, M.P. 159°-162° C prepared according to the method of IKEHARA et al.

(7) 2-[9-(2-chloropropyl-6-purinylamino]-benzoic acid, M.P. (Kofler) 255°-260° C (methanol/dimethylformamide at 20%) starting from anthranilic acid and 9-(2-chloropropyl)-6-chloropurine, (oil), itself prepared by chlorinating 9-(2-hydroxypropyl)-6-chloropurine in an excess of $SOCl_2$.

(8) 2-[9-(4-hydroxybutyl)-6-purinylamino]-benzoic acid, M.P. 184°-188° C (ethanol/dimethylformamide, 90/10) starting from anthranilic acid and 9-(4-hydroxybutyl)-6-chloropurine, (oil), itself prepared starting from 4-(4-hydroxybutyl)-amino-5-amino-6-chloropyrimidine.

(9) 2-[9-(4-chlorobutyl)-6-purinylamino]-benzoic acid, M.P. 179°-183° C (dioxane), starting from anthranilic acid, and 9-(4-chlorobutyl)-6-chloropurine, (oil), itself prepared by chlorinating 9-(4-hydroxybutyl)-6-chloropurine in an excess of $SOCl_2$.

(10) 2-(1-β-hydroxyethylpyrazolo[3,4,d]pyrimidin-4-ylamino)-benzoic acid, M.P. 216°-220° C (anhydrous dimethylformamide) starting from anthranilic acid and 1-β-hydroxyethyl-4-chloropyrazolo[3,4,d]pyrimidine, M.P. 93°-95° C, itself prepared according to the method described in the British Pat. No. 1,284,084, starting from β-hydroxyethylhydrazine and 5-formyl-4,6-dichloropyrimidine, itself prepared according to the method of KLOETZER and HERBERZ, Monatsh. 96 (5), 1567 (1965).

(11) 2-(1-β-chloroethylpyrazolo[3,4,d]pyrimidin-4-ylamino)-benzoic acid, M.P. 214°-217° C (anhydrous dimethylformamide), starting from anthranilic acid and 1-β-chloroethyl-4-chloro-pyrazolo[3,4,d]pyrimidine, M.P. 65°-69° C, itself prepared by chlorinating 1-β-hydroxyethyl-4-chloropyrazolo[3,4,d]pyrimidine in an excess of $SOCl_2$.

(12) 2-(9-β-chloroethyl-6-purinylamino)-4-chloro benzoic acid, M.P. 203°-207° C (dimethylformamide/water 50/50), starting from 2-amino-4-chloro benzoic acid and 9-β-chloroethyl-6-chloropurine.

(13) 2-(9-β-chloroethyl-6-purinylamino)-4-methyl benzoic acid, M.P. 218°-224° C (dimethylformamide/methanol 50/50), starting from 2-amino-4-methyl benzoic acid and 9-β-chloroethyl-6-chloropurine.

(14) 2-(9-β-methoxyethyl-6-purinylamino)-benzoic acid, M.P. 230°-231° C (2/3 methanol/1/3 ethanol) starting from anthranilic acid and 9-β-methoxyethyl-6-chloropurine, M.P. 84°-85° C.

(15) 2-(9-β-methylthioethyl-6-purinylamino)-benzoic acid, M.P. 187°-191° C (n. butanol), starting from anthranilic acid and 9-β-methylthioethyl-6-chloropurine, M.P. 60°-63° C

(16) 2-[9-(5-hydroxypentyl)-6-purinylamino]-benzoic acid, M.P. 182°-186° C (anhydrous dioxane), starting from anthranilic acid and 9-(5-hydroxypentyl)-6-chloropurine, M.P. 75°-78° C.

(17) 2-[9-(5-chloropentyl)-6-purinylamino]-benzoic acid, starting from anthranilic acid and 9-(5-chloropentyl)-6-chloropurine (oil)

(18) d 2-[9-(3-hydroxy-2-propyl)-6-purinylamino]-benzoic acid, starting from anthranilic acid and l 9-(3-hydroxy-2-propyl)-6-chloropurine, M.P. 199°-201° C, $a_D^{25} = -4,3°$ (c=0,5 $CH_3OH$).

(19) d 2-[9-(3-chloro-2-propyl)-6-purinylamino]-benzoic acid, M.P. 158°-161° C, $a_D^{26} = +4,5°$ (c=1DMSO), starting from anthranilic acid and l 9-(3-chloro-2-propyl)-6-chloropurine, M.P. 87°-79° C, $a_D^{26} = -10,1°$ (c=0,5 $CH_3OH$).

(20) d 2-[9-(4-hydroxy-3-butyl)-6-purinylamino]-benzoic acid, starting from anthranilic acid and l 9-(4-hydroxy-3-butyl)-6-chloropurine.

(21) d 2-[9-(4-chloro-3-butyl)-6-purinylamino]-benzoic acid, starting from anthranilic acid and l 9-(4-chloro-3-butyl)-6-chloropurine.

(22) d 2-[9-(4-hydroxy-2-methyl-3-butyl)-6-purinylamino]-benzoic acid, starting from anthranilic acid and l 9-(4-hydroxy-2-methyl-3-butyl)-6-chloropurine, M.P. 85°-87° C, $a_D^{25} = -18°$ (c=1 $CH_3OH$).

(23) d 2-[9-(4-chloro-2-methyl-3-butyl)-6-purinylamino]-benzoic acid, starting from anthranilic acid and 1 9-(4-chloro-2-methyl-3-butyl)-6-chloropurine.

(24) dl 2-[9-(4-hydroxy-2-methyl-3-butyl)-6-purinylamino]-benzoic acid, M.P. of its dihydrochloride : 222°–226° C with decomposition, starting from anthranilic acid and dl 9-(4-hydroxy-2-methyl-3-butyl)-6-chloropurine, M.P. 106°–108° C.

(25) dl 2-[9-(4-chloro-2-methyl-3-butyl)-6-purinylamino]-benzoic acid, starting from anthranilic acid and dl 9-(4-chloro-2-methyl-3-butyl)-6-chloropurine, M.P. 67°–69° C.

(26) d 2-[9-(5-hydroxy-2-methyl-4-pentyl)-6-purinylamino]-benzoic acid, starting from anthranilic acid and l 9-(5-hydroxy-2-methyl-4-pentyl)-6-chloropurine, M.P. 130°–132° C, $\alpha_D^{24} = -34°$ (c=1 CHCl$_3$).

(27) d 2-[9-(5-chloro-2-methyl-4-pentyl)-6-purinylamino]-benzoic acid, starting from anthranilic acid and l 9-(5-chloro-2-methyl-4-pentyl)-6-chloropurine.

(28) 2-[9-(2-hydroxybutyl)-6-purinylamino]-benzoic acid, starting from anthranilic acid and 9-(2-hydroxybutyl)-6-chloropurine.

(29) 2-[9-(2-chlorobutyl)-6-purinylamino]-benzoic acid, starting from anthranilic acid and 9-(2-chlorobutyl)-6-chloropurine.

(30) 2-[9-(2-hydroxypentyl)-6-purinylamino]-benzoic acid, starting from anthranilic acid and 9-(2-hydroxypentyl)-6-chloropurine.

(31) 2-[9-(2-chloropentyl)-6-purinylamino]-benzoic acid, starting from anthranilic acid and 9-(2-chloropentyl)-6-chloropurine.

(32) 2,3-dihydroxypropyl 2-[9-(2-chloropropyl)-6-purinylamino]-benzoate, starting from 2,3-dihydroxypropyl 2-amino benzoate and 9-(2-chloropropyl)-6-chloropurine.

(33) l 2-[9-(3-hydroxy-2-propyl)-6-purinylamino]-benzoic acid, starting from anthranilic acid and d 9-(3-hydroxy-2-propyl)-6-chloropurine.

(34) l 2-[9-(3-chloro-2-propyl)-6-purinylamino]-benzoic acid, starting from anthranilic acid and d 9-(3-chloro-2-propyl)-6-chloropurine.

The following examples illustrate the pharmaceutical compositions containing as active ingredient, a compound of the general formula I.

EXAMPLE 35

Formulation for one ampule injectable by intravenous route:
Sodium 2-[9-(2-chloropropyl)-6-purinylamino]-benzoate . . . 0.020 g
Propylene glycol . . . 2ml
Water for injectable preparations q.s.p. . . . 5ml

EXAMPLE 36

Formulation for one tablet:
2-[9-(2-chloropropyl)-6-purinylamino]-benzoic acid . . . 0.100g
microcristalline cellulose . . . 0.071g
lactose . . . 0.071g
polyvidone carrier . . . 0.025g
carboxymethyl starch . . . 0.020g talc . . . 0.010g
magnesium stearate . . . 0.003g

We claim:
1. A compound selected from the group consisting of:
(A) heterocyclic compounds of the formula I

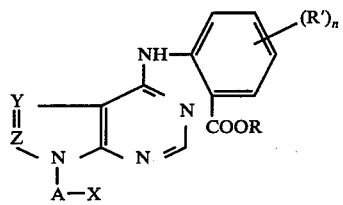

wherein:
one of Y and Z is CH and the other is nitrogen;
A is selected from the group consisting of straight and branched saturated acyclic hydrocarbon chains having from 2 to 6 carbon atoms inclusive;
X is selected from the group consisting of chlorine, hydroxy, alkoxy and alkylthio each having from 1 to 5 carbon atoms inclusive;
R is selected from the froup consisting of hydrogen, alkyl, hydroxyalkyl and dihydroxyalkyl each having from 1 to 3 carbon atoms inclusive;
R' is selected from the group consisting of halogen, alkyl and alkoxy each having from 1 to 3 carbon atoms inclusive, and
n is selected from the group consisting of 0, 1 and 2; and
(B) physiologically tolerable addition salts thereof.

2. Compounds of claim 1 for which Y is nitrogen and Z is CH.

3. A compound of claim 1 wchich is 2-[9-(2-chloropropyl)-6-purinylamino]-benzoic acid.

4. A compound of claim 1 which is 2-(9-β-chloroethyl-6-purinylamino)-benzoic acid.

5. A compound of claim 1 which is 2-(9-β-chloroethyl-6-purinylamino)-4-chlorobenzoic acid.

6. A compound of claim 1 which is d 2-[9-(3-chloro-2-propyl)-6-purinylamino]-benzoic acid.

7. A compound of claim 1 which is 2-[9-(2-chlorobutyl)-6-purinylamino]-benzoic acid.

8. A pharmaceutical composition, in unit dosage form, useful in treating convulsions and like CNS disorders of a depressive nature, containing as active ingredient a compound of claim 1 in an amount of 10 to 200 mg together with a suitable pharmaceutical carrier therefor.

9. A method for treating a living animal body afflicted with convulsions or like central nervous system disorders of a depressive nature, comprising the step of administering an amount of a compound of claim 1 in an amount which is effective for the alleviation of the said condition.

10. A pharmaceutical composition, in unit dosage form, useful in treating convulsions and like CNS disorders of a depressive nature, comprising a pharmaceutically-acceptable carrier and a compound according to claim 1 as active ingredient in an amount effective for the said purpose, at least 10 mg per unit dosage form.

* * * * *

UNITED STATES PATENT AND TRADEMARK OFFICE
CERTIFICATE OF CORRECTION

PATENT NO. : 4,100,286
DATED : July 11, 1978
INVENTOR(S) : Regnier et al.

It is certified that error appears in the above-identified patent and that said Letters Patent are hereby corrected as shown below:

[54] Title; "AMINE)BENZOIC ACIDS" should read --AMINO)BENZOIC ACIDS--
Col. 5, Example 7, line 1; "(2-chloropropyl" should read --(2-chloropropyl)--

Signed and Sealed this

Sixteenth Day of January 1979

[SEAL]

Attest:

RUTH C. MASON
Attesting Officer

DONALD W. BANNER
Commissioner of Patents and Trademarks